United States Patent [19]

Schulman et al.

[11] Patent Number: 4,716,886
[45] Date of Patent: Jan. 5, 1988

[54] UMBILICAL CORD CLAMP AND CUTTERS

[75] Inventors: Norman M. Schulman, Los Angeles; Donald Raible, Irvine, both of Calif.

[73] Assignee: Norman Schulman, Los Angeles, Calif.

[21] Appl. No.: 858,397

[22] Filed: May 1, 1986

[51] Int. Cl.$^4$ .............................................. A61B 17/08
[52] U.S. Cl. ................................. 128/305; 128/346; 128/326; 30/124
[58] Field of Search ............... 128/305, 346, 326, 319, 128/320; 30/136, 124

[56] References Cited

U.S. PATENT DOCUMENTS

| | | | |
|---|---|---|---|
| 600,887 | 3/1898 | Pettit . | |
| 1,710,766 | 12/1927 | Dilworth . | |
| 2,052,870 | 2/1936 | Coco | 128/346 |
| 2,323,183 | 9/1942 | Alleyne | 128/361 |
| 2,434,831 | 4/1946 | Brandenburg | 128/346 |
| 2,498,372 | 2/1950 | Kortlucke, Jr. et al. | 128/305 |
| 2,524,337 | 10/1950 | Whittaker | 128/305 |
| 3,040,749 | 4/1958 | Payton | 128/346 |
| 3,106,919 | 10/1963 | Churchville | 128/305 |
| 3,566,873 | 3/1971 | Melges | 128/305 |
| 3,631,858 | 1/1972 | Ersek | 128/318 |
| 3,706,312 | 12/1972 | Melges | 128/305 |
| 4,026,294 | 5/1977 | Mattler | 128/305 |
| 4,428,374 | 1/1984 | Auburn | 128/318 |
| 4,572,181 | 2/1986 | Mattler | 128/305 |
| 4,576,165 | 3/1986 | Green et al. | 128/305 |

Primary Examiner—Dalton L. Truluck
Assistant Examiner—Denise Whelton
Attorney, Agent, or Firm—Spensley Horn Jubas & Lubitz

[57] ABSTRACT

A disposable double-clamp device for severing an umbilical cord while maintaining the severed ends thereof in a clamp. Two clamps are held together in a side-by-side relation by a shear pin. A cutting blade is located between the abutting clamps, its forward cutting motion being impeded by said shear pin. After the device is brought into a clamped position, further pressure is exerted upon the blade, which breaks the shear pin. A wedge on the blade provides outward lateral pressure to the two clamps, thereby stretching the umbilical conduit at the end of the cut as well as provide for clamp separation. The blade's cutting edge then easily cuts and severs the umbilical cord. Further downward pressure causes the wedge to separate both clamps, with the ends of each portion of the severed cord being clamped by one of the pair of clamps.

21 Claims, 9 Drawing Figures

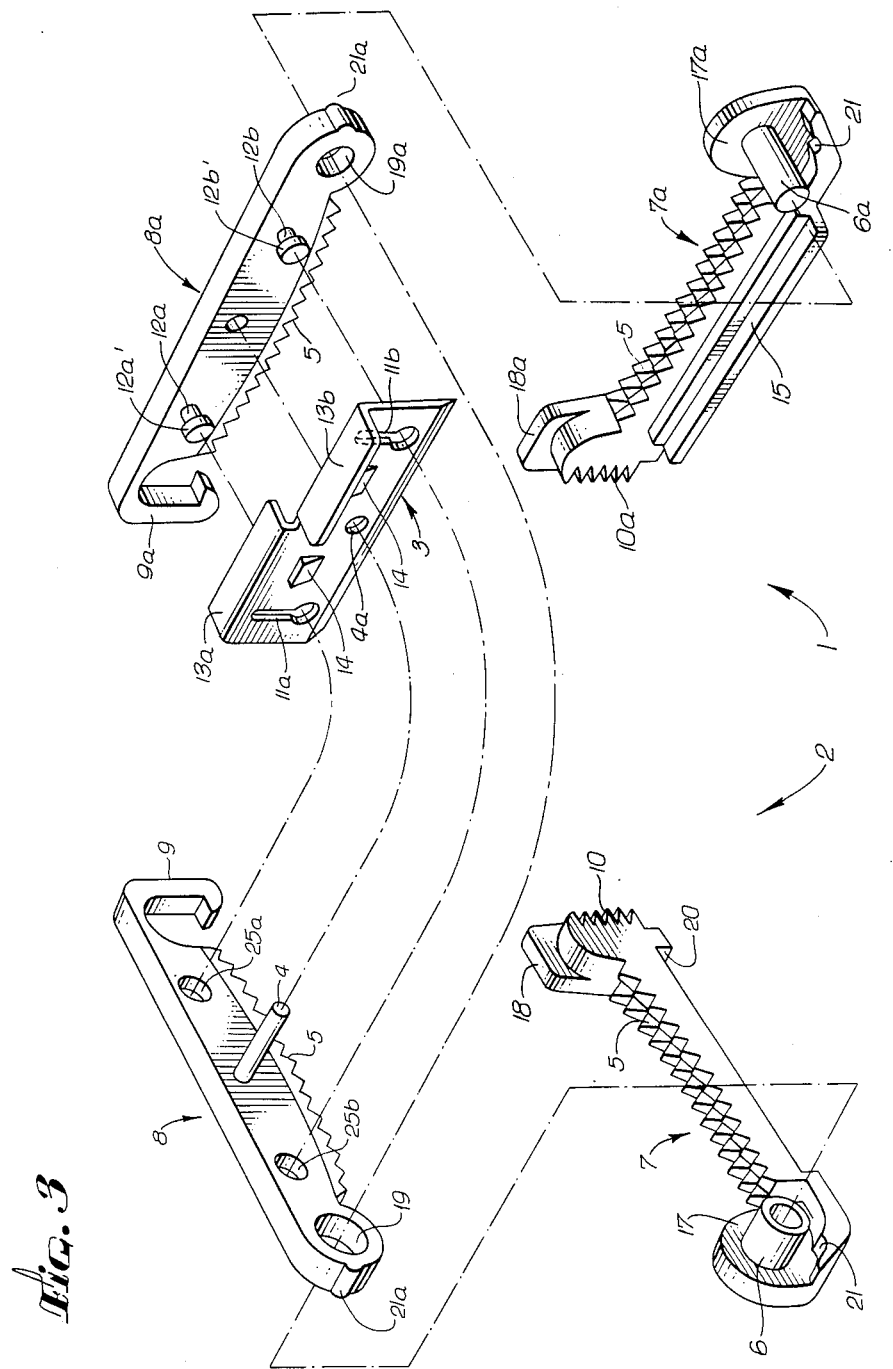

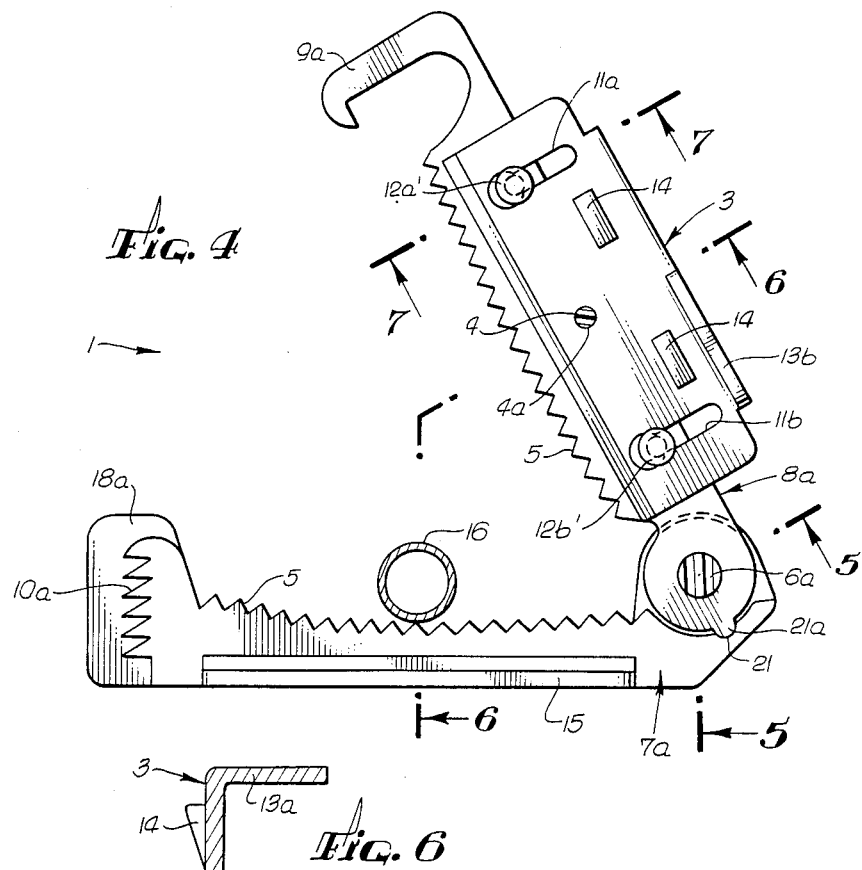
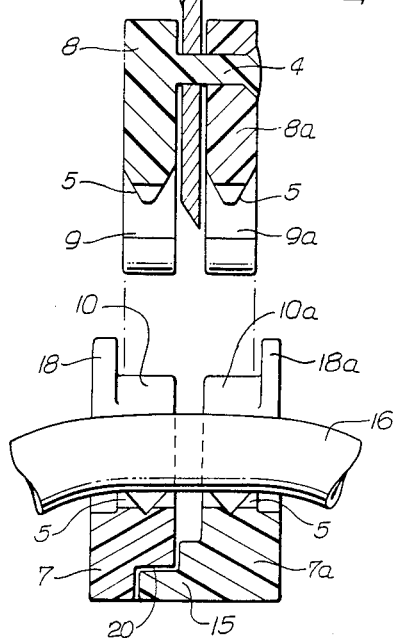
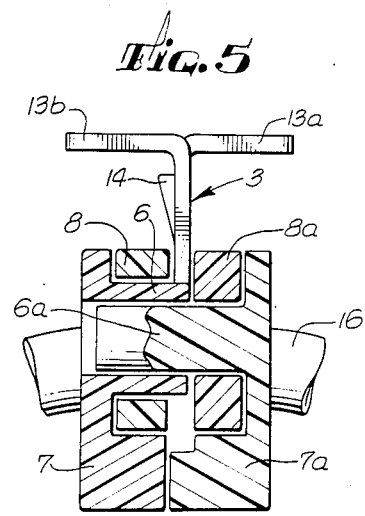

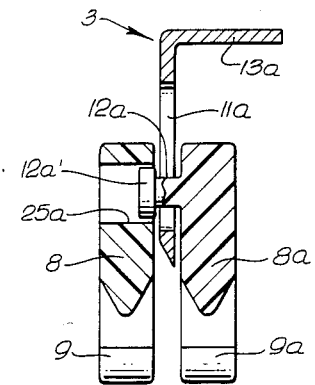
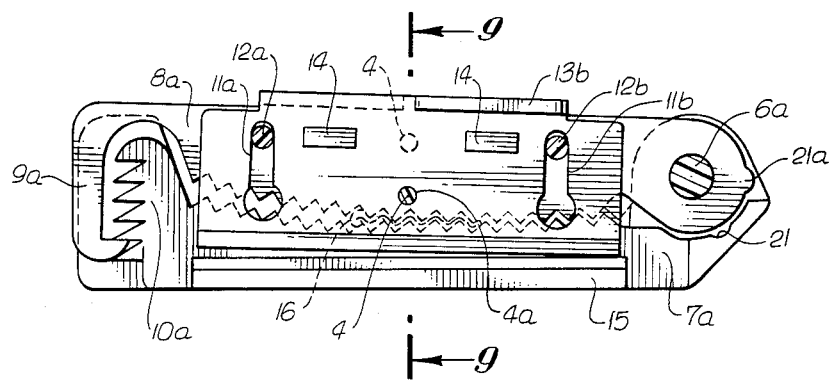
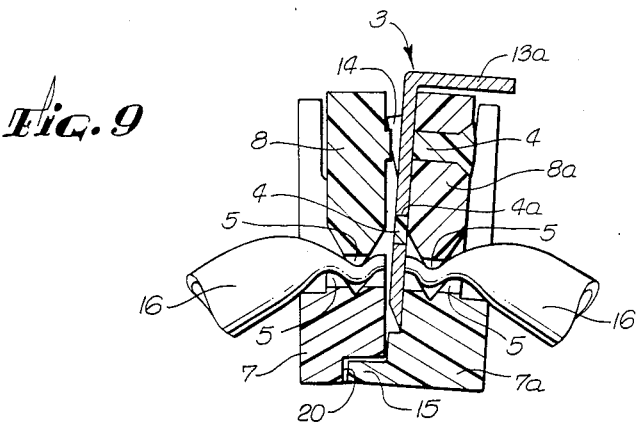

ing both clamps to close about the cord. Further squeezing causes the blade, in the area of the shear pin hole, to be pressed downward against the shear pin, which breaks. Then, the cutting edge of the blade comes into contact with the umbilical cord and severs it. Toward the end of the cutting operation, the wedge on the blade forces, through outward spreading of the two clamps to separate, maintaining their clamped positions about the two severed ends of the umbilical cord.

As can be seen, the advantage of the present invention over the prior art is its ability to permit clamping, cutting, and separating of the cord in substantially one single motion, while maintaining clamps about both ends of the severed cord.

UMBILICAL CORD CLAMP AND CUTTERS

BACKGROUND OF THE INVENTION

The present invention relates to a medical clamp and cutter of tubular bodies, particularly to a clamp and cutter for umbilical cords.

The umbilical cord is a tubular structure which connects a fetus with the placenta. The cord permits the exchange of waste products, oxygen and nutrients between the mother and her fetus. Upon the baby's birth, a traditional method of severing the umbilical cord would involve the use of two clamps for clamping the cord at two points and a cutting blade for severing the cord between the two clamped points.

The above traditional method was time consuming, cumbersome and costly. As a result, various double clamp devices have been suggested for simultaneously clamping and cutting the umbilical cord. After severing the cord, however, these devices require an additional step to separate the placenta from the fetus while maintaining their respective clamped positions. For example, reference is made to the prior art devices disclosed in Whittaker, U.S. Pat. Nos. 2,524,337, Churchville, 3,106,919; Hurley, Jr., 3,323,208; and Mattler, 4,026,294. Each of these devices suffer from the disadvantage of requiring an additional step after cutting and clamping for separating the device. This additional step may be both time consuming and cumbersome, the disadvantages of which may be accentuated in an emergency situation when life and death may be determined by a matter of seconds.

An object of the present invention is to provide an improved double-clamp device which is able to simultaneously sever an umbilical cord while maintaining each severed end in a clamp.

Another object of the present invention is to provide a double-clamp device, which is inexpensive to produce, thereby permitting the device to be provided cost and effectively disposed of after each use.

SUMMARY OF THE INVENTION

In accordance with the present invention, these and other objectives are achieved in the following manner. The present invention's double-clamp device employs a pair of clamps in a side-by-side abutting relation, each clamp comprising a pair of arms, one upper and one lower, each pair of arms being connected by a hinge at one end and a latch at the other end for keeping the clamp in a clamped position. One of the clamps, the cutting clamp, is connected to a cutting blade through a pair of attached slot pins which sit in a pair of inverted keyhole slots in the blade. The blade sits in a ready cutting position with each slot pin guided in the narrow neck portion of its respective keyhole slot. The blade is always sheathed between the two clamps, its cutting plane being along the plane separating the two clamps. The blade also contains a spreading wedge, which helps separate the two clamps at the end the cutting operation. Maintaining the clamps in a side-by-side relationship is a shear pin, which goes through a shear pin hole in the cutting blade and connects the upper arms of each clamp.

In accordance with the operation of the present invention, the double-clamp device is placed into position about the umbilical cord. After the device is so placed, the following operations are effected in substantially one motion. First, the device is squeezed together causing both clamps to close about the cord. Further squeezing causes the blade, in the area of the shear pin hole, to be pressed downward against the shear pin, which breaks. Then, the cutting edge of the blade comes into contact with the umbilical cord and severs it. Toward the end of the cutting operation, the wedge on the blade forces, through outward spreading of the two clamps to separate, maintaining their clamped positions about the two severed ends of the umbilical cord.

BRIEF DESCRIPTION OF THE DRAWINGS

A detailed description of the invention will be made with reference to the accompanying drawings, wherein like numerals designate corresponding parts in the several figures.

FIG. 3 is an exploded view of the double-clamp device.

FIG. 4 is a lateral view of the device with the first clamp broken off to show the cutting blade.

FIG. 5 is a sectional view of the device at the hinge pin taken from FIG. 4.

FIG. 6 is a sectional view of the device at the shear pin taken from FIG. 4.

FIG. 7 is a sectional view of the device at the keyhole slot and pin joint of the cutting blade taken from FIG. 4.

FIG. 8 is the same broken lateral view of FIG. 3 showing the device after cutting the umbilical cord, and while separating the two clamps.

FIG. 9 is a sectional view taken from FIG. 8, showing the double-clamp device being separated into two clamps by the cutting blade's wedge, while each clamp remains clamped onto the severed ends of the cord.

DESCRIPTION OF THE PREFERRED EMBODIMENT

Figure 1:
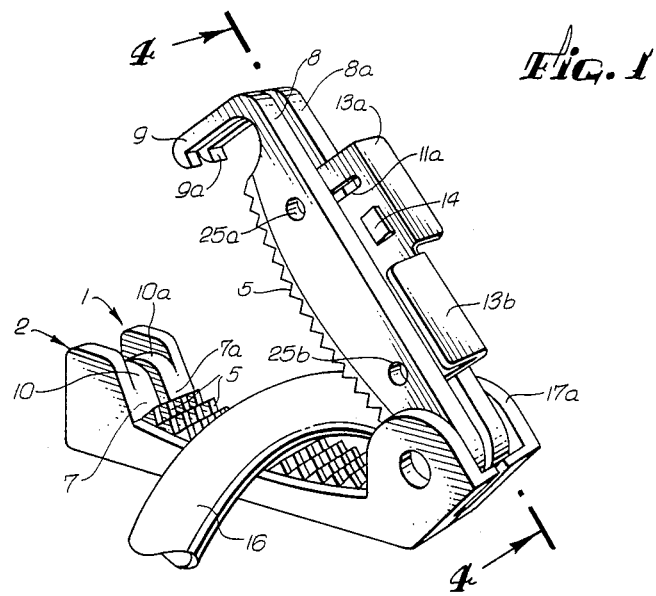
FIG. 1 is a prospective view of the double-clamp device of the present invention prior to cutting.
Figure 2:
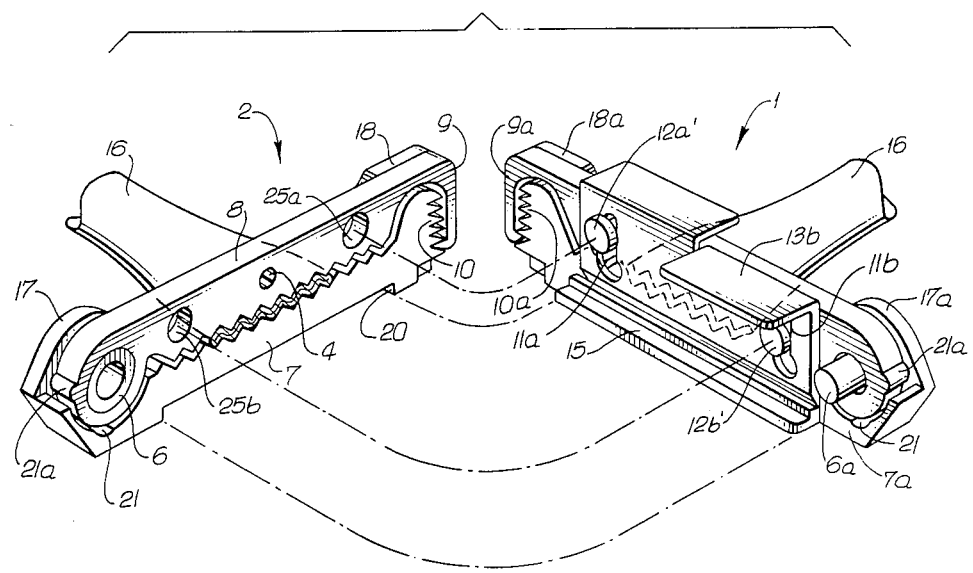
FIG. 2 is a prospective view of the double-clamp device after clamping, cutting, and separating.

FIG. 1 shows the double-clamp device of the present invention. The double-clamp device consists of clamp 1 in a side-by-side abutting relation with clamp 2. As seen in FIG. 2, clamp 1 is identical in nearly all aspects with clamp 2. Clamps 1 and 2 are joined together side-by-side by a single shear pin 4 joining the upper arms 8,8a as shown in FIG. 3. Other means for selectively joining clamps 1 and 2 together are within the scope of the present invention. For example, another shear pin could extend from and join lower arms 7,7a.

As seen in FIG. 3, clamps 1 and 2 are each comprised of a pair of elongated lower arms 7,7a and elongated upper arms 8,8a. Each pair of upper and lower arms are preferably configured so that they are curved and the upper arm jaws mate with the lower arm jaws, having a series of serrations 5 either perpendicular to the length of the arms or at an angle on their adjacent faces. When arms 7,7a and 8,8a are clamped together, their curvatures and teeth mesh together for excellent gripping ability.

Arms 7,7a and 8,8a are connected at one end by pivot pins 6,6a and barrel openings 19,19a, which together form a pair of pin-barrel hinges. Pivot pins 6,6a are each integrally connected to backwalls 17,17a of lower arms 7,7a. In addition, as seen in both FIGS. 3 and 6, pivot pin 6 is hollow so that pivot pin 6a slidingly fits into pivot pin 6, thereby providing further stability to the two clamps while in a side-by-side position. However, pins 6,6a are designed so that they can be readily separated.

In the preferred embodiment, arms 7,7a each define a small detent 21 into which protrusion 21a on arms 8,8a extends. This is illustrated in FIG. 2. Protrusion 21a and detent 21 are positioned such that the arms 8,8a are selectively retained in an open position forming an angle of about 40 to about 80 degrees with respect to arms 7,7a.

Connected at the other end of arms 7,7a and 8,8a, as seen in FIG. 3, are latching means, 9,9a, and associated receiving means, 10,10a. Latching means 9,9a are integrally connected to upper arms 8,8a, and are preferably configured like hooks, the bent lips being flat and at acute angles. Receiving means 10,10a are preferably serrated, with rows of flat surfaced teeth, so that latching means 9,9a may matingly latch onto different levels of teeth. Receiving means 10,10a are each integrally connected to backwalls 18,18a of lower arms 7,7a.

As shown in FIGS. 2 and 3, cutting blade 3 is disposed in a slot formed between clamps 1 and 2 so that cutting takes place along the plane separating clamps 1 and 2. Blade 3 is movingly connected to upper arm 8a through a pair of pin-slot guides. In the preferred embodiment, blade 3 contains a pair of inverted keyhole slots, 11a,11b, and arm 8a contains a pair of slot pins, 12a,12b having slot pin heads 12a',12b'. Slot pin heads 12a',12b' are configured so that they are unable to pass through slots 11a,11b. Other means for movingly connecting blade 3 to arm 8a are within the scope of the present invention. Heads 12a' and 12b' extend into holes 25a and 25b, respectively on arm 8. This configuration helps increase stability of the device.

As shown in FIGS. 2 and 7, during its cutting action, blade 3 moves down slots 11a,11b, guided by pins 12a,12b while being retained by slot pin heads 12a',12b'. Pressure for cutting is enhanced by a pair of outwardly facing right angle handles, 13a,13b, atop of blade 3, which provide a greater surface area for hand pressure. In addition, as best seen in FIG. 2, shelf 15 joined to arm 7a acts like a cutting board, providing a resisting force aginst the cord to assist in the cutting operation of blade 3.

In the preferred embodiment, as seen in FIG. 3, shelf 15 is integrally attached to lower arm 7a, which is part of the same clamp to which cutting blade 3 is attached. Lower arm 7 includes a longitudinal opening or slot 20 configured so as to matingly fit and register with shelf 15 when the two clamps are in a side by side position. Slot 20 and shelf 15 act to maintain stability of the device, and more particularly lower arms 7,7a. As noted above, an additional pin could be used to join arms 7,7a so as to further increase stability.

During the cutting action of blade 3, as shown in FIG. 9, wedge 14 of blade 3 provides a separating force between clamps 1 and 2. In the preferred embodiment, as best seen in FIG. 1, wedge 14 is formed by an outwardly extending protrusion on cutting blade 3. Other methods of creating wedge 14, including the attachment of a separate part, is included within the scope of this invention.

Clamps 1 and 2 are each preferably molded as unitary units from a nontoxic, sterilizable inexpensive plastic material. The plastic material should be sufficiently rigid so that the clamps easily engage into a secure clamped position. Other types of material for the clamps are within the scope of the present invention. The shear pin joining the two clamps may be molded as an integral part of upper clamp 9 (FIG. 3) or as a separate pin made of any rigid material that can be easily broken by the application of squeezing pressure from one's hand. The shear pin material, however, should withstand any lesser pressure to ensure clamp closure.

The operation of the present invention will now be explained in greater detail.

FIG. 4 shows the double-clamp device just prior to clamping about umbilical cord 16. Once the device is in position, as indicated in FIG. 4, it is ready for the simultaneous clamping, cutting and separating of umbilical cord 16. As the arms 7 and 8 are closed together, the device is secured about the cord 16 as shown in FIG. 8. In order to help maintain the cord in a desired location, arms 7,7a and 8,8a are curved and serrated. As the arms close about cord 16, the latching and receiving means 9,9a and 10,10a engage. The cord 16 is now firmly held in place at two distinct locations; to wit: between arms 7 and 8 and 7a and 8a.

As seen in FIG. 6, further squeezing of the device causes cutting blade 3 to move downward, causing blade 3, in the area of shear pin hole 4a, to confront and break shear pin 4. Clamps 1 and 2 are now maintained in a side-by-side position by the force applied to the clamps and the umbilical cord 16, the squeezing force applied to the clamp maintains the clamps together by the interlocking or mating of shelf 15 with slot 20 and the heads 12a',12b' and holes 25a,b.

As blade 3 continues to travel downward towards the end of the cut, wedge 14 begins to apply outward lateral pressure to clamps 1 and 2. At the end of the cut umbilical cord 16 becomes stretched taut by the lateral outward pressure from wedge 14 and further by the clamps beginning to separate, thereby making the cord easier to cut. As blade 3 cuts cord 16, shelf 15 provides the necessary resisting force to the cutting pressure. After cord 16 is completely severed, as seen in FIG. 9, lateral pressure from wedge 14 completely separates clamps 1 and 2, shelf 15 being easily disengaged from slot 20. During this procedure, heads 12a',12b' and holes 25a,b as well as pivot pins 6,6a are being urged to separate.

As seen in FIG. 2, each clamp maintains its clamped position about each end of the severed umbilical cord. In addition, as seen in FIG. 8, blade 3 is locked into its final position by squeezing pressure which moves the blade 3 down the narrow neck regions of slots 11a,11b onto slot pins 12a,12b and behind heads of these pins. In an alternate configuration, handle 13 has a depending protrusion which engages a slot formed in the top of arm 7 or 8. Yet other means for locking blade 3 in place once it is depressed is also within the scope of this invention.

The above description of a presently preferred embodiment of the invention was intended to illustrate by way of example the novel features that are believed to be characteristics of the present invention. It is to be expressly understood, however, that the specific embodiment is for the purpose of illustration and description only, and is not intended as a definition of the limits of the invention. Other embodiments of the invention are therefore included within the scope of this invention.

What is claimed is:

1. A double-clamp device for the clamping and severing of a tubular body, each severed end thereof being retained in a clamp, comprising:

a pair of clamps, each clamp comprising a pair of arms hingably connected at one end and further having latching means for securing said pair of arms in a clamped position about said tubular body wherein said latching means secures said pair of arms in a clamped position prior to severing the tubular body;

breakable connecting means disposed between said pair of clamps for selectively connecting and maintaining said pair of clamps in a side-by-side abutting relation; and a cutting blade for breaking said connecting means and severing said tubular body, located between said clamps and adjacent said breakable connecting means, said cutting blade integrally connected to one of said arms and movable relative thereto, whereby clamping and severing of said tubular body is done substantially in a single motion with each end of said severed tubular body remaining clamped.

2. The device as claimed in claim 1 wherein said breakable connecting means is a pin joined to each of said pair of clamps.

3. The device as claimed in claim 1 wherein said arms include curved serrated portions.

4. The device as claimed in claim 1 wherein said pair of clamps defines a slot through which said cutting blade extends.

5. The device as claimed in claim 1 wherein one of said clamps further comprises an outwardly extending cutting shelf.

6. A double-clamp device for severing an umbilical cord while retaining each severed end thereof in a clamp, comprising:

a pair of clamps, each clamp comprising a pair of elongated arms integrally connected at one end, one of said arms further including stabilizing guide means for stabilizing and guiding a cutting blade for movement relative thereto, said pair of arms further having latching means for securing said pair of arms in a clamped position about said cord wherein said latching means secures said pair of arms in a clamped position prior to severing the tubular body;

breakable connecting means disposed between said pair of clamps for selectively maintaining said pair of clamps in a side-by-side abutting relation; and a cutting blade, disposed adjacent said breakable connecting means, for breaking said connecting means and for severing said umbilical cord, said blade being movable relative to said stabilizing guide means and integrally connected thereto such that the motion of said blade with respect to one of said arms is selectively limited.

7. The device as claimed in claim 6 wherein said connecting means is a breakable pin.

8. The device a claimed in claim 6 wherein one of said clamps includes a shelf for resisting cutting pressure from said blade.

9. The device as claimed in claim 6 wherein said blade further comprises a pair of outwardly facing handles for applying squeezing pressure.

10. The device as claimed in claim 6 wherein said pair of arms is integrally connected at one end by a pair of hinging means, each hinging means comprising a pivotable pin-barrel joint.

11. The double-clamp device as claimed in claim 6 wherein said cutting blade further includes a wedge for spreading apart said pair of clamps.

12. A method for severing the umbilical cord or similar body conduit and for retaining each severed end in a clamp, comprising the steps of:

(a) providing a double-clamp device, which comprises:

a pair of clamps, each clamp comprising a pair of arms hingably connected at one end and further having latching means disposed between said pair of clamps for securing said pair of arms in a clamped position about said body conduit; breakable connecting means for sselectively connecting and maintaining said pair of clamps in a side-by-side abutting relation; and a cutting blade for breaking said connecting means and severing said body conduit, disposed adjacent said breakable connecting means and between said clamps, said cutting blade integrally connected to one of said arms and movable relative thereto;

(b) squeezing said double-clamp device into a clamped position about said body conduit such that said arms are clamped together;

(c) breaking said breakable connecting means by said cutting blade;

(d) cutting and severing said body conduit with said cutting blade; and (e) separating said pair of clamps, each clamp remaining in a clamped position about each severed end of said body conduit, and wherein steps (c) and (d) are performed substantially in a single motion.

13. A double-clamp device for the clamping and severing of a tubular body, each severed end thereof being retained in a clamp, comprising:

a pair of clamps, each clamp comprising a pair of arms hingably connected at one end and further having latching means for securing said pair of arms in a clamped position about said tubular body;

breakable connecting means disposed between said pair of clamps for selectively connecting and maintaining said pair of clamps in a side-by-side abutting relation; and a cutting blade for breaking said connecting means and severing said tubular body, located between said clamps adjacent said breakable connecting means, said cutting blade integrally connected to one of said arms and movable relative thereto, said cutting blade further include an opening for said breakable connecting means, wherein clamping and severing of said tubular body is done substantially in a single motion with each end of said severed tubular body remaining clamped.

14. The double-clamp device of claim 13 wherein the breakable connecting means passes thpough the opening in said cutting blade.

15. A double-clamp device for severing an umbilical cord while retaining each severed end thereof in a clamp, the device comprising:

a pair of clamps, each clamp comprising a pair of arms integrally connected at one end, at least one of said arms having stabilizing guide means for stabilizing and guiding the movement of a cutting blade relative therto, said pair of arms further having latching means for securing said pair of arms in a clamped position about said core;

breakable connecting means disposed between said pair of clamps for selectively maintaining said pair of clamps in a side-by-side abutting relationship; and a cutting blade, disposed adjacent said breakable connecting means, for breaking said breakable connecting means and for severing said umbilical core, said cutting blade being joined to said stabilizing guide means and movable with respect thereto, wherein the blade further includes an opening and said breakable connecting means through said opening.

16. The device of claim 15 wherein said breakable connecting means comprises a sheer pin integrally attached to one arm of one of the clamps.

17. The double-clamp device of claim 16 wherein the sheer pin is integrally attached to one arm of both of the clamps.

18. A double-clamp device for severing an umbilical cord while retaining each severed end thereof in a clamp, comprising:

a pair of clamps, each clamp comprising an upper arm and a lower arm, said arms being integrally connected at one end, at least one of said arms having stabilizing guide means for stabilizing and guiding the movement of a cutting blade relative thereto, said pair of arms further having latching means for securing said pair of arms in a clamped position about said cord prior to the severing of said cord, and wherein said pair of clamps are initially joined together such that independent motion of one of said clamps relative to the other is substantially precluded;

breakable connecting means, disposed between said pair of clamps, for selectively maintaining said pair of clamps in a side-by-side abutting relationship; and a cutting blade, disposed adjacent said breakable connecting means, for severing said umbilical cord and for breaking said breakable connecting means, said cutting blade being joined to said stabilizing guide means and movable with respect thereto, wherein the blade further includes an opening and said breakable connecting means passes through said opening.

19. The double-clamp device of claim 18 wherein said breakable connecting means comprises a sheer pin integrally attached to one of the arms of one of the clamps.

20. The double-clamp device of claim 19 wherein said sheer pin is integrally attached to one arm of both of the clamps.

21. The double-clamp device of claim 13 wherein said latching means secures said pair of arms in a clamped position prior to severing the tubular body.

* * * * *